(12) United States Patent
Scherer

(10) Patent No.: US 10,039,770 B2
(45) Date of Patent: Aug. 7, 2018

(54) PROSTAGLANDIN F2ALPHA AND ANALOGUES THEREOF FOR TREATING ATROPHIC CUTANEOUS SCARRING

(71) Applicant: Galderma S.A., Lausanne, Grey (CH)

(72) Inventor: Warren J. Scherer, Lutz, FL (US)

(73) Assignee: Galderma S.A., Lausanne (CH)

( * ) Notice: Subject to any disclaimer, the term of this patent is extended or adjusted under 35 U.S.C. 154(b) by 0 days.

(21) Appl. No.: 15/021,789

(22) PCT Filed: Sep. 26, 2014

(86) PCT No.: PCT/IB2014/002746
§ 371 (c)(1),
(2) Date: Mar. 14, 2016

(87) PCT Pub. No.: WO2015/044788
PCT Pub. Date: Apr. 2, 2015

(65) Prior Publication Data
US 2016/0228453 A1    Aug. 11, 2016

Related U.S. Application Data

(60) Provisional application No. 61/960,740, filed on Sep. 26, 2013.

(51) Int. Cl.
*A61K 9/127* (2006.01)
*A61K 31/5575* (2006.01)
*A61K 45/06* (2006.01)
*A61K 9/00* (2006.01)

(52) U.S. Cl.
CPC ........ *A61K 31/5575* (2013.01); *A61K 9/0014* (2013.01); *A61K 45/06* (2013.01)

(58) Field of Classification Search
CPC .... A61K 2300/00; A61K 31/573; A61K 9/48; A61K 45/06; A61K 2039/505; A61K 2039/54; A61K 31/4439; A61K 47/12; A61K 47/26; A61K 47/38; A61K 9/19; A61K 9/10; A61K 9/16; A61K 31/5575; A61K 31/167; A61K 31/195; A61K 31/352; A61K 31/385; A61K 31/498
USPC .......................................................... 424/450
See application file for complete search history.

(56) References Cited

U.S. PATENT DOCUMENTS

| | | |
|---|---|---|
| 2012/0251613 A1 | 10/2012 | Jain et al. |
| 2014/0079686 A1* | 3/2014 | Barman ............... A61K 8/4953 424/94.67 |
| 2014/0323558 A1* | 10/2014 | Old ..................... C07D 333/40 514/448 |

* cited by examiner

*Primary Examiner* — Nannette Holloman
(74) *Attorney, Agent, or Firm* — Sunit Talapatra

(57) ABSTRACT

A method of treating atrophic cutaneous scarring in humans is claimed. The method involves the topical application of a therapeutic amount of prostaglandin F2-alpha (PGF 2α) or a PGF 2α analog directly to the area of atrophic scarring.

11 Claims, 3 Drawing Sheets

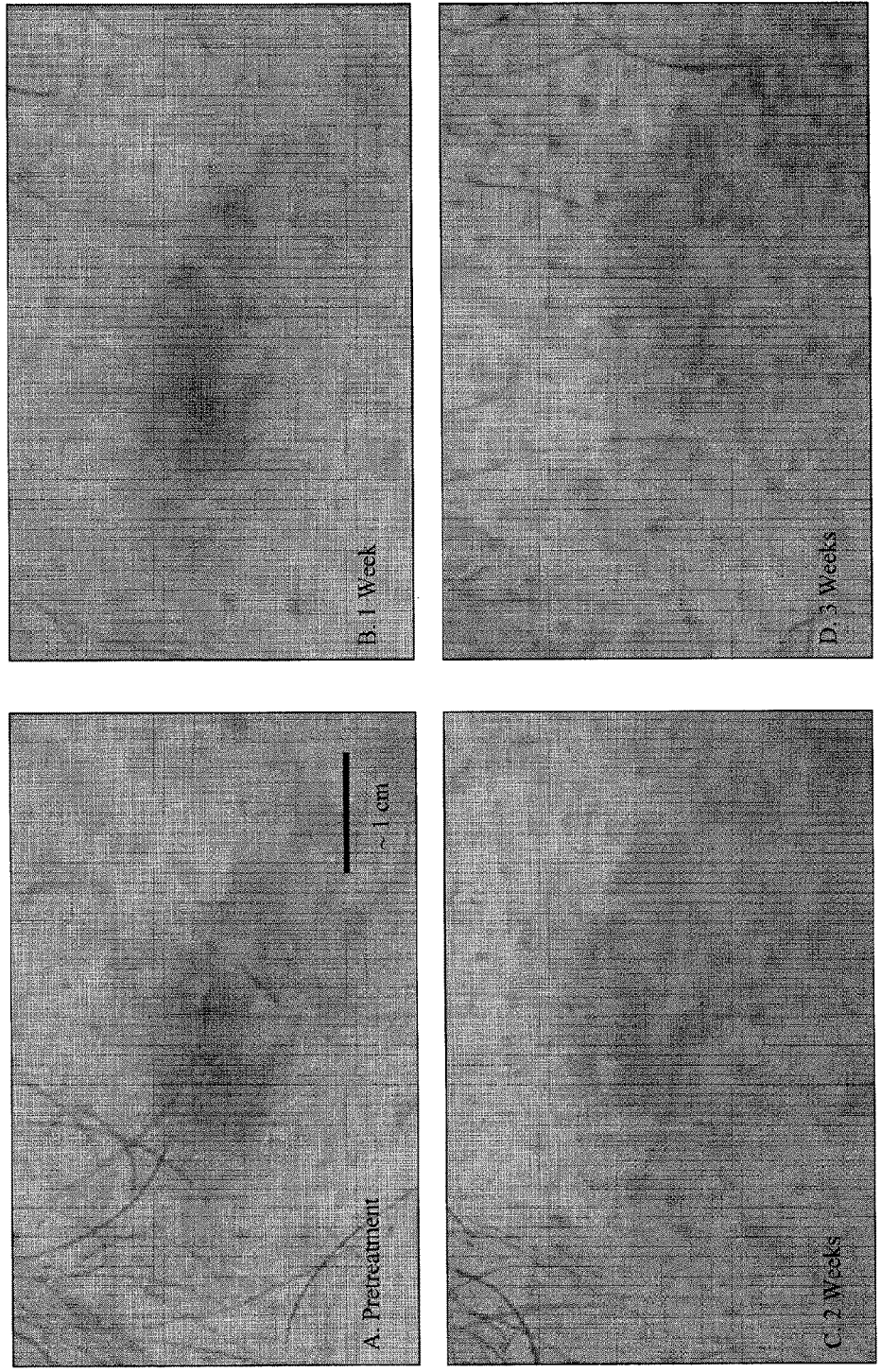

Figure 1. A - D: Effect of PGF 2α analog on atrophic scarring. A: 6 month old atrophic abdominal scar prior to treatment. B through D: Following gentle exfoliation with a cotton cloth and mild detergent, travaprost 0.004% solution was digitally massaged on to the surface of the scar once daily. Images show the appearance of the scar after each week of treatment. Over time, the atrophic base of the scar gradually undergoes fibrosis and fills with collagen. No changes in the surrounding skin are noted. (WJ Scherer: METHODS AND COMPOSITIONS FOR TREATING ATROPHIC CUTANEOUS SCARRING)

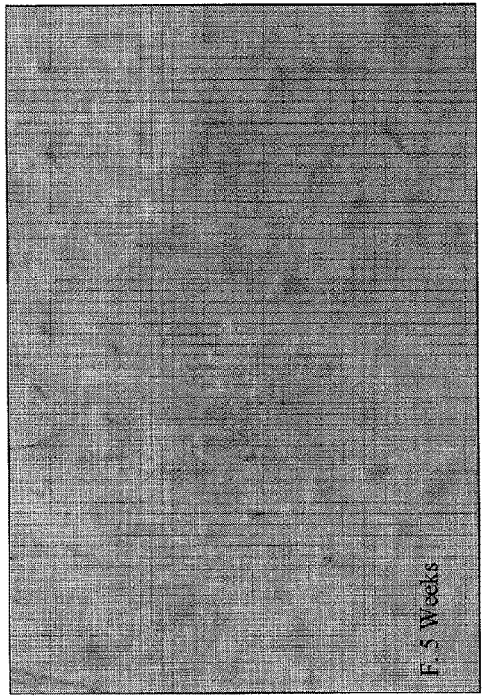
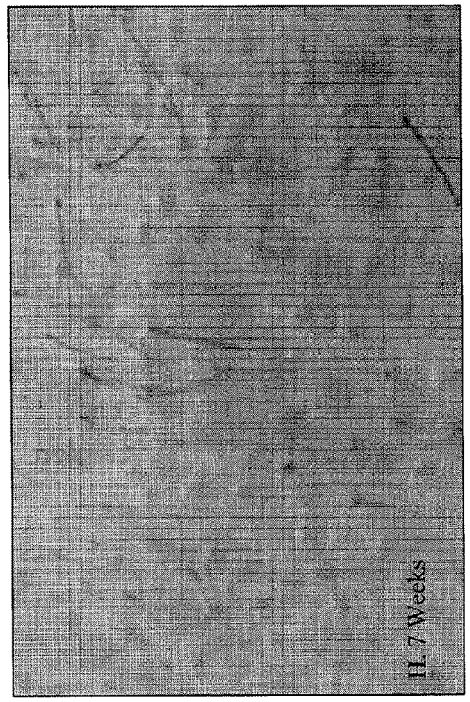
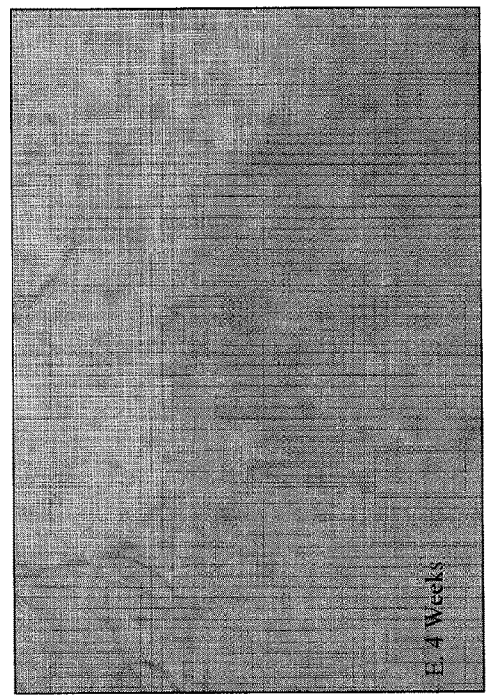
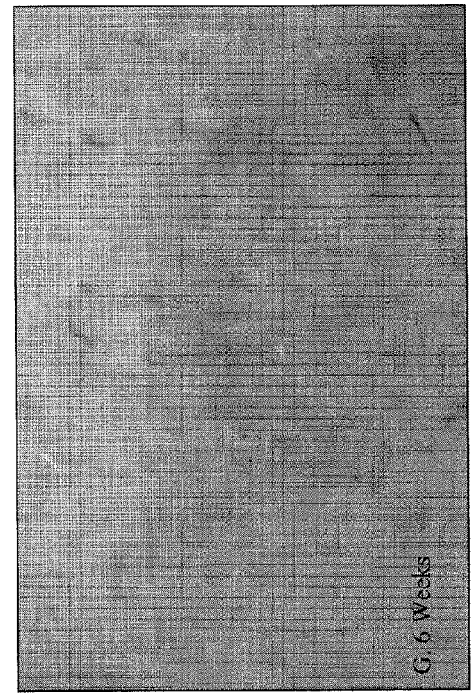

Figure 1. E - H: Effect of PGF 2α analog on atrophic scarring. E through H: Following gentle exfoliation with a cotton cloth and mild detergent, travaprost 0.004% solution was digitally massaged on to the surface of the scar once daily. Images show the appearance of the scar after each week of treatment. Over time, the atrophic base of the scar gradually undergoes fibrosis and fills with collagen. No changes in the surrounding skin are noted. (WJ Scherer: METHODS AND COMPOSITIONS FOR TREATING ATROPHIC CUTANEOUS SCARRING)

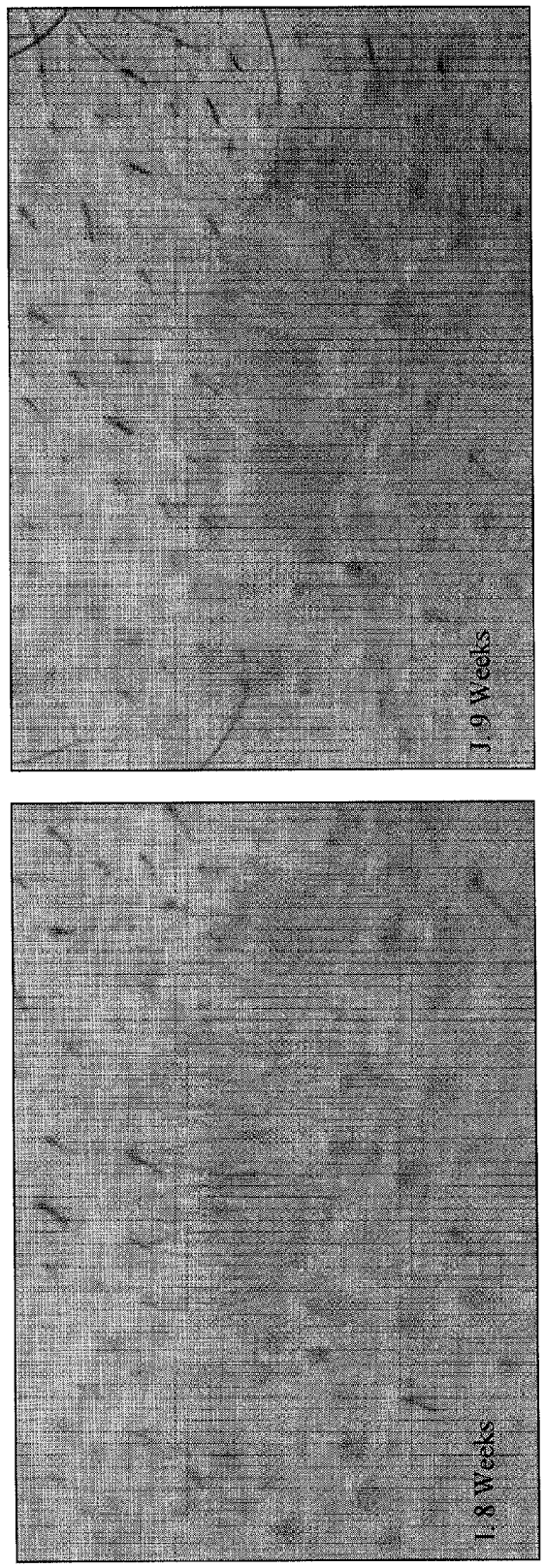

Figure 1. I - J: Effect of PGF 2α analog on atrophic scarring. I through J: Following gentle exfoliation with a cotton cloth and mild detergent, travaprost 0.004% solution was digitally massaged on to the surface of the scar once daily. By 8 weeks, normal appearing Langer lines begin to form across the scarred area. No changes in the surrounding skin, such as keloid, atrophy or pigmentation are noted. (WJ Scherer: METHODS AND COMPOSITIONS FOR TREATING ATROPHIC CUTANEOUS SCARRING)

PROSTAGLANDIN F2ALPHA AND ANALOGUES THEREOF FOR TREATING ATROPHIC CUTANEOUS SCARRING

CROSS-REFERENCE TO RELATED APPLICATION

This application asserts priority to an International Application filed under the Patent Cooperation Treaty, PCT/IB2014/002746, filed Sep. 26, 2014, which claims the benefit of U.S. Provisional Patent Application No. 61/960,740 filed Sep. 26, 2013. Each of the foregoing applications is herein incorporated by reference in its entirety.

FIELD OF THE INVENTION

The present invention relates generally to compositions and methods for treating, inhibiting and reducing cutaneous atrophic scarring in a human in need of such treatment. More specifically, the present invention describes methods and pharmaceutically active compositions containing prostaglandin F 2α (PGF 2α) analogs for the topical treatment, inhibition and reduction of atrophic cutaneous scarring in a human in need of such treatment.

BACKGROUND OF THE INVENTION

Cutaneous scars are areas of fibrous tissue, or fibrosis, that replaces normal skin following injury. Scars result from the biological wound repair processes of the body. After an injury, a clot or provisional wound matrix forms. Specialized cells called fibroblasts migrate to the provisional wound matrix and act to close the wound. This is accomplished by the production of extracellular collagen by fibroblasts. Although the collagen composition of scar tissue is similar to the tissue that it replaces, the collagen fibers of scar tissue are often variably expressed and are organized and cross-linked in a parallel direction rather than the "basket weave" orientation of normal skin tissue. Additionally, cutaneous scar tissue does not contain the adnexal structures such as hair follicles, sebaceous glands and sweat glands that are present in normal skin.

Due to the variable expression or over-expression of collagen by fibroblasts, cutaneous scars can assume different phenotypes. These include atrophic (or hypotrophic) scars, hypertrophic scars and keloids.

Atrophic scars have the appearance of depressions or recesses that lie below the surface of the surrounding skin (aka "sunken scarring"). They occur when underlying structures such as fat or muscle, are lost due to injury along with insufficient production of new collagen fibers at the base of the scar. Atrophic scarring is commonly associated with acne, infection (eg: *Varicella zoster* or *Stapphylococcus*), surgery or accidental trauma. Atrophic scars often appear red because of dermal thinning and increased visibility of the underlying capillary network.

Hypertrophic scarring occurs when fibroblasts over-produce collagen during the healing process. This causes the scar to be raised above the surrounding skin. Hypertrophic cutaneous scars are common following surgical wound closure or traumatic skin injuries.

Keloids are considered to be a more severe form of hypertrophic scarring. Keloids continue to grow into large, benign neoplasms. Keloids are more common in dark-skinned people. They can occur following surgery, trauma, acne or body piercing. They tend to occur on the shoulders and chest and are more common in wounds closed by granulation tissue, a.k.a. second intention. The remainder of this description will be limited to the discussion of atrophic type of cutaneous scar and its treatment.

Because patients with atrophic cutaneous scarring seek to improve the appearance and texture of their skin, treatments have been developed to address this issue. The clinical objective behind treating atrophic scarring is to physically raise the depressed area of scarring to the same physical level as the surrounding skin, therefore allowing a smoother transition between the scar and the normal skin. Treatments that are currently in use include injectable soft tissue fillers, collagen induction therapy, chemical reconstruction of skin scars (CROSS) therapy, laser treatment and transplantation of autologous fibroblasts.

Injectable dermal fillers are substances that are injected into the depressed areas of atrophic scars. The currently approved substances used as fillers consist of collagen, hyaluronic acid, poly-L-lactic acid, polymethylmethacrylate with bovine collagen, calcium hydroxylapatite or autologous fibroblasts. Although injections of these substances result in cosmetic improvement of atrophic scars, the effect is temporary and patients require repeat injections over time. Additional side effects of fillers include uneven skin contour and allergic reactions.

The principle underlying collagen induction therapy is to stimulate fibroblasts at the base of the atrophic scar to produce collagen in an attempt to fill the recessed area. Collagen induction therapy utilizes the technique of microneedling, often administered via microneedle rollers applied directly to the scar. This treatment produces small punctures in the skin that act to stimulate fibroblasts to produce collagen in response to the trauma. The collagen will then act to thicken the bed of the scar, raising it to the level of the surrounding normal skin. Collagen induction therapy has been met with varying amounts of success. Aside from pain during the procedure, risks include infection and bleeding. Additionally, multiple treatments are typically required.

Chemical reconstruction of skin scars (CROSS) therapy consists of applying full concentration trichloroacetic acid to atrophic scars. The acid produces a localized cutaneous chemical injury. Similar to collagen induction therapy, CROSS therapy attempts to use targeted injury to stimulate fibroblasts to increase collagen production in the injured areas. Risks include infection and multiple treatments are typically required.

Ablative laser treatment with a carbon dioxide or Er:YAG laser is also used to treat atrophic cutaneous scars. The principle behind laser treatment is to smooth the transition between the depressed borders of atrophic scars and the normal surrounding skin. This serves to make the scarred skin areas appear less noticeable. The laser can also be used to treat the bed of the atrophic scar. The rationale is that laser injury will stimulate fibroblasts to produce collagen that will then fill in the damaged areas. Unfortunately, laser treatment is painful, requires multiple treatments and can be very costly.

There is currently no available medical therapy for treating atrophic cutaneous scars that does not involve localized, trauma-induced stimulation of collagen production by fibroblasts. The present disclosure describes methods and compositions for treating atrophic cutaneous scars in humans via stimulation of fibroblast collagen production using the topical application of PGF 2α analogs admixed in a pharmaceutically suitable vehicle.

SUMMARY OF THE INVENTION

The present invention provides methods and compositions for treating, reducing or inhibiting atrophic cutaneous scarring in humans by stimulating fibroblast collagen production via the topical application of therapeutically effective amounts of such composition to the atrophic scar for a sufficient period of time. Fibroblast collagen production may be stimulated by stimulation of the cellular FP receptors. The compositions consist of one, or an effective combination of PGF 2α analogs admixed in a pharmaceutically suitable vehicle.

The PGF 2α analogs of the invention include PGF 2α, latanoprost, travoprost, bimatoprost and tafluprost, and are usually present alone or in combination in the compositions in an amount from about 0.001% to 0.5% by weight. Another preferred concentration is 0.001% to 0.20% by weight of the composition.

The compositions may also include a sunscreen, sunblock, moisturizer, preservative, antibacterial agents, anthelmintic agents, antioxidant agents, steroidal anti-inflammatory agents, non-steroidal anti-inflammatory agents, antiangiogenic agents, and derivatives of retinoic acid.

The compositions may be formulated as a gel, emulsion, ointment, spray, aqueous solution or suspension, liposomes or nanospheres.

In order to treat erythema associated with atrophic scars, the compositions may further include an alpha-1 or alpha-2 adrenergic agonist known to cause vascular constriction such as oxymetazoline, tetrahydrozoline, naphazoline, xylometazoline, phenylephrine, methoxamine, mephentermine, metaraminol, desglymidodrine, midodrine, brimonidine, and the pharmaceutically acceptable salts thereof, and any combination of such compounds or salts.

The methods and compositions presently described may be used before, during or after administration of established, standard-of-care therapies for atrophic scarring such as, but not limited to injectable soft tissue fillers, collagen induction therapy, chemical reconstruction of skin scars (CROSS) therapy, silicone sheets or gels, pressure dressings and laser treatment.

In one embodiment, the invention relates to a method of treating atrophic cutaneous scarring in a human in need thereof by topical administration of a pharmaceutical composition including a therapeutically effective amount of prostaglandin F 2-alpha (PGF 2α), a PGF 2α analog, or combinations thereof, and a pharmaceutically acceptable carrier to the site of the atrophic cutaneous scarring. Preferably, the PGF 2α analog is latanoprost, travoprost, bimatoprost, or tafluprost. The PGF 2α and PGF 2α analog concentration is preferably from about 0.001% to 0.20% by weight of said composition.

The pharmaceutical composition may further include a UVA/UVB sunscreen with either an SPF range of 10 to 75+ or a UVA protection grade range of 2+ to 8+. The pharmaceutical composition may further include an alpha-1 or alpha-2 adrenergic analog or a pharmaceutically acceptable salt thereof, and combinations thereof. Preferred alpha-1 or alpha-2 adrenergic analogs are oxymetazoline, tetrahydrozoline, naphazoline, xylometazoline, phenylephrine, methoxamine, mephentermine, metaraminol, desglymidodrine, midodrine, and brimonidine.

The pharmaceutical composition may further include a moisturizing agent. The pharmaceutical composition may also be a slow release vehicle formulation such as a liposome, nanosphere, gel, ointment, or emulsion.

The pharmaceutical composition may be administered before, during or after a percutaneous collagen induction therapy, ablative laser treatment, non-ablative laser treatment, dermabrasion therapy, application of a human amniotic membrane graft, a chemical peel, application of a semi-occlusive silicone-based ointment, gel or sheet or other elastic pressure dressing, application of trichloroacetic acid, injection of a dermal filler, or transplantation of autologous fibroblasts to the area(s) of atrophic scarring.

These and other aspects of the invention will be better understood by reading the following detailed description and appended claims.

DETAILED DESCRIPTION OF THE INVENTION

Cutaneous scarring occurs as a result of injury to the skin and deposition of extracellular collagen by fibroblasts at the site of the wound. Cutaneous scarring characterized by depressions or recesses that lie below the surface of the surrounding skin is referred to as atrophic scarring. Atrophic scars occur when underlying structures such as fat or muscle, are lost due to injury accompanied by insufficient production of new collagen fibers at the base of the scar. Atrophic scarring is commonly associated with acne, infection (eg: *Varicella zoster* or *Stapphylococcus*), surgery or accidental trauma. Atrophic scars often appear red because of dermal thinning and increased visibility of the underlying capillary network. The objective of treating atrophic scars is centered around elevating the depressed area of the scar to the level of the surrounding normal skin by using injectable fillers, or attempting to stimulate collagen production by fibroblasts via traumatic techniques such as percutaneous microneedling, chemical injury and laser injury.

Prostaglandin F 2α (PGF 2α) and its analogs act by stimulating cellular FP receptors and have a profound effect on fibroblasts and the extracellular environment in normal and pathological states.

Drawing 1: structures of PGF 2α, latanoprost, travoprost, bimatoprost and tafluprost.

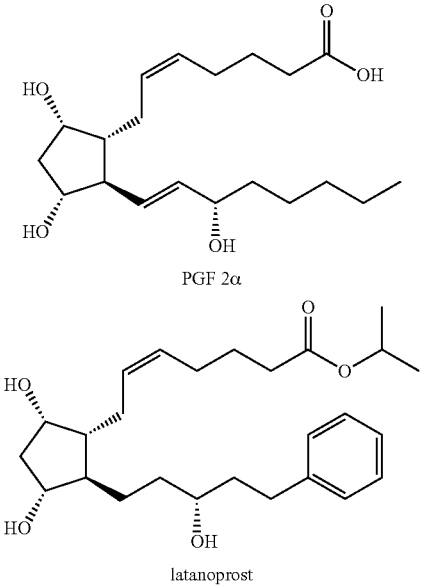

PGF 2α latanoprost

-continued

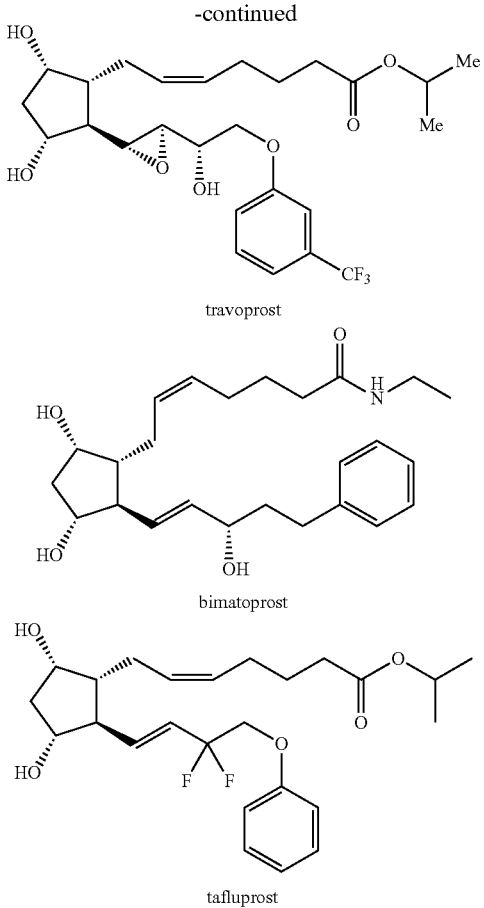

travoprost bimatoprost tafluprost

In ophthalmology, PGF 2α analogs such as latanoprost, travoprost, bimatoprost and tafluprost have been safely used for treating glaucoma for well over a decade. Normal eye pressure is maintained via the proper drainage of aqueous fluid through the trabecular and uveoscleral outflow pathways of the eye. On a cellular level, it has been shown that PGF 2α analogs topically applied to the eye stimulate the activation of matrix metalloproteinases, resulting in the remodeling of the extracellular matrix of the uveoscleral outflow pathway for aqueous humor. Matrix metalloproteinases are enzymes that act to break down components of the extracellular matrix. In the eye, this PGF 2α analog-induced extracellular matrix remodeling decreases resistance to aqueous flow through the uveoscleral pathway, resulting in a lowering of intraocular pressure. Furthermore, it has been demonstrated in cell culture that PGF 2α analogs influence the growth of human dermal fibroblasts.

In a mouse model of bleomycin-induced systemic sclerosis (Sc), the mechanism of collagen production by skin (Sc)fibroblasts is complex. In this model, collagen production requires that the enzyme plasmin-α2-antiplasmin (α2AP) binds to the enzyme adipose triglyceride lipase (ATGL). The α2AP-ATGL complex then activates calcium independent phospholipase A2 (iPLA(2)) to produce PGF 2α. The PGF 2α then stimulates transforming growth factor β (TGF β) production by (Sc)fibroblasts. TGF β then acts to stimulate collagen production and fibrosis. It was recently discovered that in a strain of mice with a mutated form of α2AP, bleomycin-induced collagen production by (Sc) fibroblasts was attenuated. It was then discovered that fibrosis (i.e. collagen production) in this mutant (Sc)fibroblast strain could be reestablished by administering exogenous PGF 2α. Exogenous PGF 2α then reversed the attenuation and this resulted in dermal thickening and fibrosis. However, this study did not address the effectiveness of specific PGF 2α analogs on the model system.

Another example of the profibrotic properties of PGF 2α has been demonstrated by Bastiaansen-Jenniskens et al in a human culture model of osteoarthritis. These investigators found that in culture, PGF 2α, but not transforming growth factor β, stimulated synovial fibroblast collagen production, cell proliferation and cell migration.

Given these examples, it has been presently discovered that topical application of PGF 2α analogs are also efficacious in the treatment and reduction of atrophic cutaneous scars in humans. It is possible that atrophic scars are composed of fibroblasts that, because of an unknown enzymatic mutation or transformation, are unable to produce sufficient amounts of collagen. Collagen production is then "rescued" via administration of exogenous PGF 2α or PGF 2α analogs. It is also possible that exogenous PGF 2α or PGF 2α analogs simply stimulate expression of collagen in otherwise normal fibroblasts contained within atrophic cutaneous scars. These profibrotic mechanisms are speculated, as the specific biochemical make-up of fibroblasts in various types of cutaneous scars has not been researched.

Examples of improvement in atrophic cutaneous scarring imparted by use of the compositions of the present invention include:
  a. Decrease in depression of the scar bed
  b. Visibly enhanced fibrosis of previously atrophic areas of the scar
  c. Smoother transition of the border between scar tissue and the surrounding normal skin
  d. Improved coloration and decreased erythema of the scar tissue It is anticipated that the methods and compositions described in the present disclosure may be used in conjunction with common methods and treatments of atrophic scarring that currently comprise the dermatologic "standard of care". These methods and treatments include, but are not limited to CROSS therapy, collagen induction therapy, ablative and non-ablative laser treatment, dermal fillers, dermabrasion and autologous fibroblast transplantation.

The methods and compositions presently described may be used before, during or after administration of CROSS therapy using full concentration trichloroacetic acid or collagen induction therapy using cutaneous microneedling with a device such as, but not limited to a microneedle dermal roller. In this case, collagen induction therapy via microneedling or application of trichloroacetic acid could improve drug delivery to the fibroblasts in the atrophic scar and could act synergistically with PGF 2α analogs to promote collagen production by fibroblasts.

The methods and compositions presently described may be used before, during or after administration of ablative or non-ablative laser treatment of atrophic cutaneous scars. Non-ablative laser treatments include the use of a laser such as, but not limited to, a 585 nm pulsed dye laser, 1320 nm Nd:YAG laser, or 1540 nm Er:Glass laser.

The methods and compositions presently described may be used before, during or after administration of dermabrasion therapy of atrophic cutaneous scars. In this case, dermabrasion is postulated to improve drug delivery and PGF 2α analogs could act synergistically with laser treatment to promote collagen production by fibroblasts.

The methods and compositions presently described may be used before, during or after injection of dermal fillers such as, but not limited to collagen, hyaluronic acid, poly-L-lactic acid, polymethylmethacrylate with bovine collagen, or calcium hydroxylapatite. It is anticipated that the compositions described would aid the production of collagen by fibroblasts overlying the fillers and would decrease or eliminate the need for repeat injections.

The methods and compositions presently described may be used before, during or after transplantation of autologous fibroblasts for the treatment of atrophic cutaneous scars. In this case, it is postulated that PGF 2α analogs comprising the composition would also be effective in stimulating collagen production from autologously transplanted fibroblasts.

Hypertrophic scars are often treated with overlying silicone sheets, gels or pressure dressings to help flatten the collagen of the scar and promote a smooth transition between the scar and surrounding normal skin. The methods and compositions presently described may be used before, during or after application of silicone sheets, gels or pressure dressings to aid in flattening the collagen and promoting a smooth transition between the scar and surrounding normal skin.

In order to treat erythema associated with atrophic scars, the compositions may further include an alpha-1 or alpha-2 adrenergic agonist known to cause vascular constriction such as oxymetazoline, tetrahydrozoline, naphazoline, xylometazoline, phenylephrine, methoxamine, mephentermine, metaraminol, desglymidodrine, midodrine, brimonidine, and the pharmaceutically acceptable salts thereof, and any combination of such compounds or salts.

In a further embodiment, the compositions may also include a sunscreen, sunblock, moisturizer, preservative, antibacterial agents, anthelmintic agents, antioxidant agents, steroidal anti-inflammatory agents, non-steroidal anti-inflammatory agents, antiangiogenic agents, and derivatives of retinoic acid.

Pharmaceutically Acceptable Carriers

In one embodiment, the compounds of the invention are delivered to the affected area of the skin by a composition comprising a pharmaceutically acceptable topical carrier. As used herein, a pharmaceutically acceptable composition is any composition that can be applied to the skin surface for topical delivery of a pharmaceutical or medicament. Topical compositions of the invention may be prepared according to well-known methods in the art. For example, an active compound that reduces cutaneous atrophic scarring may be combined with a topical carrier by methods provided in standard reference texts, such as Remington: The Science and Practice of Pharmacy, 1577-1591, 1672-1673, 866-885 (Alfonso R. Gennaro ed. 19th ed. 1995); Ghosh, T. K.; et al. Transdermal and Topical Drug Delivery Systems (1997).

The topical carriers useful for topical delivery of compounds of the invention can be any pharmaceutically acceptable carrier known in the art for topically administering pharmaceuticals. Some examples of topical carriers include solvents, such as a polyalcohol or water; suspensions; emulsions (either oil-in-water or water-in-oil emulsions), such as creams, ointments, or lotions; micro emulsions; gels; liposomes; or powders.

Emulsions and Gels as Topical Carriers

In a preferred embodiment, the topical carrier used to deliver a compound of the invention is an emulsion, e.g., a cream, lotion, or ointment; or a gel. An emulsion is a dispersed system comprising at least two immiscible phases, one phase dispersed in the other as droplets, usually ranging in diameter from 0.1 µm to 100 µm. An emulsifying agent is optionally included to improve stability. When water is the dispersed phase and oil is the dispersion medium, the emulsion is termed a water-in-oil emulsion. When oil is dispersed as droplets throughout an aqueous phase as droplets, the emulsion is termed an oil-in-water emulsion. Both are useful as carriers in the methods of the present invention. Emulsions, such as creams, ointments and lotions that can be used as topical carriers and their preparation are disclosed in Remington: The Science and Practice of Pharmacy, 282-291 (Alfonso R. Gennaro ed. 19th ed. 1995).

In one embodiment, the pharmaceutically acceptable carrier is a gel. Gels are semisolid systems that contain suspensions of inorganic particles, usually small inorganic particles, or organic molecules, usually large organic molecules, interpenetrated by a liquid. When the gel mass comprises a network of small discrete inorganic particles, it is classified as a two-phase gel. Single-phase gels consist of organic macromolecules distributed uniformly throughout a liquid such that no apparent boundaries exist between the dispersed macromolecules and the liquid. Suitable gels for use in the invention are known in the art, and may be two-phase or single-phase systems. Some examples of suitable gels are disclosed in Remington: The Science and Practice of Pharmacy, 1517-1518 (Alfonso R. Gennaro ed. $19^{th}$ ed. 1995). Other suitable gels for use with the invention are disclosed in U.S. Pat. No. 6,387,383 (issued May 14, 2002); U.S. Pat. No. 6,517,847 (issued Feb. 11, 2003); and U.S. Pat. No. 6,468,989 (issued Oct. 22, 2002).

Gelling agents, that may be used include those known to one skilled in the art, such as hydrophilic and hydroalcoholic gelling agents frequently used in the cosmetic and pharmaceutical industries. A suitable hydrophilic or hydroalcoholic gelling agent comprises "CARBOPOL®" (B.F. Goodrich, Cleveland, Ohio), "HYPAN®" (Kingston Technologies, Dayton, N.J.), "NATROSOL®" (Aqualon, Wilmington, Del.), "KLUCEL®" (Aqualon, Wilmington, Del.), or "STABILEZE®" (ISP Technologies, Wayne, N.J.).

"CARBOPOL®" is one of numerous cross-linked acrylic acid polymers that are given the general adopted name carbomer. "Carbomer" is the USP designation for various polymeric acids that are dispersible but insoluble in water. When the acid dispersion is neutralized with a base a clear, stable gel is formed. The preferred carbomer is Carbomer 934P because it is physiologically inert and is not a primary irritant or sensitizer. Other carbomers include 910, 940, 941, and 1342.

Carbomers dissolve in water and form a clear or slightly hazy gel upon neutralization with a caustic material such as sodium hydroxide, potassium hydroxide, triethanolamine, or other amine bases. "KLUCEL®" is a cellulose polymer that is dispersed in water and forms a uniform gel upon complete hydration. Other suitable gelling agents include hydroxyethylcellulose, cellulose gum, MVE/MA decadiene crosspolymer, PVM/MA copolymer, or a combination thereof.

In one embodiment, the minimum amount of gelling agent in the composition is about 0.5%, more preferably, about 0.75%, and most preferably about 1%. In another preferred embodiment, the maximum amount of gelling agent in the composition is about 2%, more preferably about 1.75%, and most preferably about 1.5%.

In another embodiment, the topical carrier used to deliver a compound of the invention is an ointment. Ointments are oleaginous semisolids that contain little if any water. Preferably, the ointment is hydrocarbon based, such as a wax, petrolatum, or gelled mineral oil. Suitable ointments for use in the invention are well known in the art and are disclosed in Remington: The Science and Practice of Pharmacy, 1585-1591 (Alfonso R. Gennaro ed. 19th ed. 1995).

The pharmaceutical carrier may also be a cream. A cream is an emulsion, i.e., a dispersed system comprising at least two immiscible phases, one phase dispersed in the other as droplets usually ranging in diameter from 0.1 μm to 100 μm. An emulsifying agent is typically included to improve stability.

The pH of the pharmaceutical carrier is adjusted with, for example, a base such as sodium hydroxide or potassium hydroxide; or an amine base, such as trimethylamine. The pH can also be adjusted with an acid, such as hydrochloric acid or acetic acid. In one embodiment, the minimum pH of the carrier is about 5, preferably 5.5, and most preferably 6.2 when the carrier is diluted by a factor of ten. The maximum pH of the carrier is about 8, preferably about 7.5, more preferably 7, and most preferably about 6.8 when the carrier is diluted by a factor of ten. Each minimum pH value can be combined with each maximum pH value to create various pH ranges. For example, the pH may be a minimum of 6.2 and a maximum of 7.5.

The pH values given above are those that occur if the composition is diluted with water by a factor of ten. It is not necessary to dilute the composition by a factor of ten in order to obtain a pH value. In practice, the composition may be diluted by any value that permits pH to be measured. For example, the composition may be diluted by a factor of about five to about twenty.

Aqueous Topical Compositions of the Invention

In another embodiment, the topical carrier used in the topical compositions of the invention is an aqueous solution or suspension, preferably, an aqueous solution or suspension. Solutions and suspensions are well-known suitable topical carriers for use in the invention. Suitable aqueous topical compositions for use in the invention are disclosed in Remington: The Science and Practice of Pharmacy 1563-1576 (Alfonso R. Gennaro ed. 19th ed. 1995). Other suitable aqueous topical carrier systems are disclosed in U.S. Pat. No. 5,424,078 (issued Jun. 13, 1995); U.S. Pat. No. 5,736,165 (issued Apr. 7, 1998); U.S. Pat. No. 6,194,415 (issued Feb. 27, 2001); U.S. Pat. No. 6,248,741 (issued Jun. 19, 2001); U.S. Pat. No. 6,465,464 (issued Oct. 15, 2002).

Tonicity-adjusting agents can be included in the aqueous topical compositions of the invention. Examples of suitable tonicity-adjusting agents include, but are not limited to, sodium chloride, potassium chloride, mannitol, dextrose, glycerin, and propylene glycol. The amount of the tonicity agent can vary widely depending on the composition's desired properties. In one embodiment, the tonicity-adjusting agent is present in the aqueous topical composition in an amount of from about 0.5 to about 0.9 weight percent of the composition.

The viscosity of aqueous solutions of the invention can be any convenient viscosity, and can be adjusted by adding viscosity adjusting agents, for example, but not limited to, polyvinyl alcohol, povidone, hydroxypropyl methyl cellulose, poloxamers, carboxymethyl cellulose, or hydroxyethyl cellulose. In one embodiment, the aqueous topical compositions of the invention have a viscosity in the range of from about 15 cps to about 25 cps.

In a preferred embodiment, the aqueous topical composition of the invention is an isotonic saline solution, optionally comprising a preservative, such as benzalkonium chloride or chlorine dioxide, a viscosity-adjusting agent, such as polyvinyl alcohol, and/or a buffer system such as sodium citrate and citric acid, or potassium acetate and acetic acid.

Excipients

The topical compositions of the invention can further comprise pharmaceutically acceptable excipients such as those listed in Remington: The Science and Practice of Pharmacy (Alfonso R. Gennaro ed. 19th ed. 1995; Ghosh, T. K.; et al. Transdermal and Topical Drug Delivery Systems, 1997, including, but not limited to, protective agents, adsorbents, demulcents, emollients, preservatives, antioxidants, moisturizers, buffering agents, solubilizing agents, and surfactants. Excipients are non-active and non-essential ingredients in the composition that do not materially affect the basic characteristics of the composition.

Suitable protective agents and adsorbents include, but are not limited to, dusting powders, zinc stearate, collodion, dimethicone, silicones, zinc carbonate, aloe vera gel and other aloe products, vitamin E oil, allatoin, glycerin, petrolatum, and zinc oxide.

Suitable demulcents include, but are not limited to, benzoin, hydroxypropyl cellulose, hydroxypropyl methylcellulose, and polyvinyl alcohol.

Suitable emollients include, but are not limited to, animal and vegetable fats and oils, myristyl alcohol, alum, and aluminum acetate.

Suitable preservatives include, but are not limited to, parabens, phenoxyethanol, quaternary ammonium compounds, such as benzalkonium chloride, benzethonium chloride, cetrimide, dequalinium chloride, and cetylpyridinium chloride; mercurial agents, such as phenylmercuric nitrate, phenylmercuric acetate, and thimerosal; alcoholic agents, for example, chlorobutanol, phenylethyl alcohol, and benzyl alcohol; antibacterial esters, for example, esters of parahydroxybenzoic acid; and other anti-microbial agents such as chlorhexidine, chlorocresol, benzoic acid and polymyxin.

Chlorine dioxide ($ClO_2$), preferably, stabilized chlorine dioxide, is a suitable preservative for use with topical compositions of the invention. The term "stabilized chlorine dioxide" is well known in the industry and by those skilled in the art. Stabilized chlorine dioxide includes one or more chlorine dioxide precursors such as one or more chlorine dioxide-containing complexes and/or one or more chlorite-containing components and/or one or more other entities capable of decomposing or being decomposed in an aqueous medium to form chlorine dioxide. U.S. Pat. No. 5,424,078 (issued Jun. 13, 1995) discloses a form of stabilized chlorine dioxide and a method for producing same, which can be used as a preservative for aqueous solutions and is useful in topical compositions of the invention. The manufacture or production of certain stabilized chlorine dioxide products is described in U.S. Pat. No. 3,278,447. A commercially available stabilized chlorine dioxide that can be utilized in the practice of the present invention is the proprietary stabilized chlorine dioxide of BioCide International, Inc. of Norman, Okla., sold under the trademark Purogene™ or Purite™. Other suitable stabilized chlorine dioxide products include that sold under the trademark DuraKlor by Rio Linda Chemical Company, Inc., and that sold under the trademark Antheium Dioxide by International Dioxide, Inc.

Suitable antioxidants include, but are not limited to, ascorbic acid and its esters, sodium bisulfite, butylated hydroxytoluene, butylated hydroxyanisole, tocopherols, and chelating agents like EDTA and citric acid.

Suitable moisturizers include, but are not limited to, glycerin, sorbitol, polyethylene glycols, urea, and propylene glycol.

Suitable buffering agents for use with the invention include, but are not limited to, acetate buffers, citrate buffers, phosphate buffers, lactic acid buffers, and borate buffers.

Suitable solubilizing agents include, but are not limited to, quaternary ammonium chlorides, cyclodextrins, benzyl benzoate, lecithin, and polysorbates.

Additional Pharmaceutical Active Compounds

In one embodiment, the only pharmaceutically active compound effective in treating, improving or reducing atrophic cutaneous scarring is a PGF 2α analog such as PGF 2α, latanoprost, travoprost, bimatoprost or tafluprost and the pharmaceutically acceptable salts thereof, and any combination of such compounds or salts.

In another embodiment, the PGF 2α analog effective in treating, improving or reducing atrophic cutaneous scarring is combined with an alpha-1 or alpha-2 adrenergic receptor agonist known to be pharmaceutically effective in reducing cutaneous erythema due to cutaneous vascular dilation when applied topically. These include agents such as, but not limited to oxymetazoline, tetrahydrozoline, naphazoline, xylometazoline, phenylephrine, methoxamine, mephentermine, metaraminol, desglymidodrine, midodrine, brimonidine, and the pharmaceutically acceptable salts thereof, and any combination of such compounds or salts.

In yet another embodiment, one or more additional pharmaceutically active ingredients are included in the compositions of the invention. Additional active ingredients may include any pharmaceutically active ingredient. For example, the one or more additional pharmaceutically active ingredients may include, but are not limited to, antibacterial agents, anthelmintic agents, antioxidant agents, steroidal antiinflammatory agents, non-steroidal antiinflammatory agents, antiangiogenic agents, and derivatives of retinoic acid.

Dosage

Dosages and dosing frequency of an effective amount of the compounds of the invention can be determined by trained medical professionals, typically during pre-clinical and clinical trials. The dosages and dosing frequency depend upon numerous factors, such as the therapeutic activity of the compounds of the invention, the characteristics of the particular topical composition, and the nature, cause, location, identity and severity of the cutaneous atrophic scarring being treated.

In general, the active compounds described above are present in a composition of the invention in a minimum amount of about 0.001%, 0.0015%, 0.004%, 0.03%, 0.05%, 0.1%, 0.2%, 0.25%, 0.3%, 0.35%, 0.4%, or 0.5% based upon the total weight of the composition. Generally, the active compounds described above are present in a composition of the invention in a maximum amount of about 5% 4%, 3%, 2%, 1%, 0.9%, 0.8%, 0.7%, or 0.6% based upon the total weight of the composition. For example, some suitable dosages of PGF 2α analogs currently used in ophthalmic solutions to treat glaucoma are 0.0015%, 0.004%, 0.005% and 0.03%.

Topical Administration

The pharmaceutical compositions of the invention may be applied directly to the affected area of the skin in any manner known in the art. For example, a solution may be applied by cotton swab or may be sprayed. A suspension or an emulsion may be applied with a q-tip or an applicator stick, or by simply spreading a composition of the invention onto the affected area with one or more fingers. Preferably, the pharmaceutical composition of the invention is applied only to skin, and is not administered to eyes or other mucous membranes.

Generally the amount of a topical composition of the invention applied to the affected skin area ranges from about 0.0001 g/cm$^2$ of skin surface area to about 0.01 g/cm$^2$, preferably, 0.001 g/cm$^2$ to about 0.003 g/cm$^2$ of skin surface area. Typically, one to four applications per day are recommended during the term of treatment. For example, the pharmaceutical compositions may be applied once per day, twice per day, three times per day, or four times per day to the affected areas.

Miscellaneous Definitions

It is to be understood that the present invention contemplates embodiments in which each minima is combined with maxima to create all feasible ranges. For example, either (1) latanoprost or a pharmaceutically acceptable salt thereof or (2) travoprost or a pharmaceutically acceptable salt thereof may be present in a composition of the invention in an amount of from about 0.001 percent to about 5 percent based upon the total weight of the composition, preferably, from about 0.005 percent to about 1 percent based upon the total weight of the composition, or more preferably, from about 0.0015 percent to about 0.5 percent based upon the total weight of the composition.

EXAMPLE

FIG. 1 A. depicts a 6 month old atrophic cutaneous scar secondary to dermatologic surgery present on the abdomen of a 50 year old male prior to treatment. During the 3 to 4 months prior to starting topical treatment with PGF 2α analog, the scar had not qualitatively changed in structure or appearance. Examination of the scar reveals dermal thinning of the scar bed along with erythema due to increased visualization of the sub-dermal vascular network and a sharp transition or border between the scar tissue and the normal surrounding skin. The scar was then treated with an aqueous solution of topical travoprost 0.004% which was digitally massaged onto the scar surface once daily for several weeks. FIGS. 1B through J depict the appearance of the same scar at one week intervals during the treatment period. A gradual increase in fibrosis and thickening of the atrophic areas of the scar are noted over 9 weeks of treatment. Also apparent are a decrease in erythema and a visibly smoother transition of the border between the scar tissue and normal surrounding skin. At 8 weeks, normal appearing Langer lines are apparent across the extent of the previously scarred skin. At all time points, the surrounding skin showed no evidence of keloid formation, atrophy or pigmentation. No other adverse reactions were noted during or after the treatment interval.

The invention claimed is:

1. A method of treating atrophic cutaneous scarring in a human in need thereof comprising topical administration of a pharmaceutical composition comprising a therapeutically effective amount of prostaglandin F 2-alpha (PGF 2α), a PGF 2α analog, or combinations thereof, and a pharmaceutically acceptable carrier to the site of the atrophic cutaneous scarring.

2. The method of claim 1, wherein the PGF 2α analog is latanoprost, travoprost, bimatoprost, or tafluprost.

3. The method of claim 1, wherein the PGF 2α and PGF 2α analog concentration is from about 0.001 to 0.20% by weight of said composition.

4. The method of claim 1, wherein the pharmaceutical composition further comprises a UVA/UVB sunscreen.

5. The method of claim 4, wherein the UVA/UVB sunscreen has either an SPF range of 10 to 75+ or a UVA protection grade range of 2+ to 8+.

6. The method of claim 1, wherein the pharmaceutical composition further comprises an alpha-1 or alpha-2 adrenergic analog or a pharmaceutically acceptable salt thereof, and combinations thereof.

7. The method of claim 6, wherein the alpha-1 or alpha-2 adrenergic analog is oxymetazoline, tetrahydrozoline, naphazoline, xylometazoline, phenylephrine, methoxamine, mephentermine, metaraminol, desglymidodrine, midodrine, or brimonidine.

8. The method of claim 1, wherein the pharmaceutical composition further comprises a moisturizing agent.

9. The method of claim 1, wherein the pharmaceutical composition is a slow release vehicle formulation.

10. The method of claim 9, wherein the slow release vehicle formulation is a liposome, nanosphere, gel, ointment, or emulsion.

11. The method of claim 1, wherein the pharmaceutical composition is administered before, during or after a percutaneous collagen induction therapy, ablative laser treatment, non-ablative laser treatment, dermabrasion therapy, application of a human amniotic membrane graft, a chemical peel, application of a semi-occlusive silicone-based ointment, gel or sheet or other elastic pressure dressing, application of trichloroacetic acid, injection of a dermal filler, or transplantation of autologous fibroblasts to the areas of atrophic scarring.

* * * * *